(12) United States Patent
Julliand et al.

(10) Patent No.: US 12,636,322 B2
(45) Date of Patent: May 26, 2026

(54) BACTERIAL STRAIN WITH HIGH CELLULOLYTIC ACTIVITY

(71) Applicants: INSTITUT NATIONAL SUPERIEUR DES SCIENCES AGRONOMIQUES DE L'ALIMENTATION ET DE L'ENVIRONNEMENT, Dijon (FR); LAB TO FIELD, Dijon (FR)

(72) Inventors: Véronique Julliand, Fontaine les Dijon (FR); Alicia Froidurot, Dijon (FR); Emmanuel Jacotot, Sennecey-les-Dijon (FR); Samy Julliand, Dijon (FR)

(73) Assignees: INSTITUT NATIONAL SUPERIEUR DES SCIENCES AGRONOMIQUES DE L'ALIMENTATION ET DE L'ENVIRONMENT, Dijon (FR); LAB TO FIELD, Dijon (FR)

( * ) Notice: Subject to any disclaimer, the term of this patent is extended or adjusted under 35 U.S.C. 154(b) by 349 days.

(21) Appl. No.: 18/570,332

(22) PCT Filed: Jun. 24, 2022

(86) PCT No.: PCT/EP2022/067411
§ 371 (c)(1),
(2) Date: Dec. 14, 2023

(87) PCT Pub. No.: WO2022/269065
PCT Pub. Date: Dec. 29, 2022

(65) Prior Publication Data
US 2025/0319142 A1 Oct. 16, 2025

(30) Foreign Application Priority Data
Jun. 25, 2021 (EP) ..................................... 21181823

(51) Int. Cl.
| | |
|---|---|
| *A61K 39/02* | (2006.01) |
| *A23K 10/18* | (2016.01) |
| *A23L 33/135* | (2016.01) |
| *A61K 35/00* | (2006.01) |
| *A61K 35/741* | (2015.01) |
| *C12N 1/20* | (2026.01) |
| *C12N 1/205* | (2026.01) |
| *C12R 1/01* | (2006.01) |

(52) U.S. Cl.
CPC ........ *A61K 35/741* (2013.01); *A61K 39/0216* (2013.01); *C12N 1/205* (2021.05); *A61K 2035/115* (2013.01); *C12R 2001/01* (2021.05)

(58) Field of Classification Search
None
See application file for complete search history.

(56) References Cited

PUBLICATIONS

Suen G et al. PLoS One 6: e18814, 2011.*
Meinhardt SW et al. Arch Microbiol 162: 329-334, 1994.*
Burnet MC et al. PLoS One 10: e0143809, 2015.*
Forano E et al. Curr Microbiol. 28: 7-14, 2017.*
Groleau et al: "Partial characterization of the extracellular carboxymethylcellulase activity produced by the rumen bacterium Bacteroides succinogenes", Canadian Journal of Microbiology, vol. 29, No. 5, p. 504-517, May 1, 1983.
Ishaq et al: "Fibrolytic Bacteria Isolated from the Rumen of North American Moose (*Alces alces*) and Their Use as a Probiotic in Neonatal Lambs", PLOS ONE, vol. 10, No. 12, Dec. 30, 2015.
Neumann et al: "Fibrobacter communities in the gastrointestinal tracts of diverse hindgut-fermenting herbivores are distinct from those of the rumen : Ecology of Fibrobacter in hindgut-fermenting herbivores", Environmental Microbiology, vol. 19, No. 9, p. 3768-3783, Aug. 24, 2017.
Raut et al: "Deciphering the unique cellulose degradation mechanism of the ruminal bacterium Fibrobacter succinogeses S85", Scientific Reports, vol. 9, No. 1, Dec. 1, 2019.

* cited by examiner

Primary Examiner — S. Devi
(74) Attorney, Agent, or Firm — WCF IP

(57) ABSTRACT

The present invention concerns a bacterial strain of *Fibrobacter succinogenes* and a composition thereof, and its use as a probiotic in order to improve the digestive fibrolysis.

7 Claims, 6 Drawing Sheets

Specification includes a Sequence Listing.

a.

b.

c.

d.

BACTERIAL STRAIN WITH HIGH CELLULOLYTIC ACTIVITY

SEQUENCE LISTING

This application includes as the Sequence Listing the complete contents of the .txt file "13500208us_sequence-_listing", created Jul. 10, 2024, containing 726 bytes, hereby incorporated by reference.

FIELD

The present disclosure relates to the field of probiotics, more particularly to the use of a particular bacterial strain to improve plant cell wall degradation.

BACKGROUND

Microorganisms living in mammals' digestive tract all together form what is known as the microbiota and play a vital role in providing energy from the diet. The microbiota has also a great impact on the host health and well-being (1).

Cellulose is a complex polysaccharide consisting of linked D-glucose units. It is a major structural component of plant cell walls and constitutes a major source of dietary fiber. Like other complex polysaccharides from plant cell walls, dietary cellulose is not digested by mammal digestive enzymes. In the rumen and the colon of ruminants or in the large intestine of monogastrics (herbivores and omnivores), cellulose can only be broken down by the enzymes produced by the microbiota (2).

Microbial cellulose utilization ultimately results in the production of short chain fatty acids (SCFAs) like acetate, propionate and butyrate in the rumen and the colon of ruminants or in the large intestine of monogastrics (2).

SCFAs represent an energy source, which is essential to herbivorous (70% of energy provided to cattle and up to 85% of energy provided to sheep (3), up to 70% of energy provided to horses (4). For omnivores, SCFAs also account for a substantial proportion of energy intake (up to 30% of energy provided to swine (5), up to 10% of energy provided to humans (6)).

In addition to energy provision for mammals, SCFAs have a number of key roles in the gastrointestinal tract among others: i) they are an energy source for colonocytes (7); ii) they have an effect on gastrointestinal motility (7); iii) they can modulate appetite and increase insulin sensitivity (7); iv) they play a part in the intestinal barrier integrity and function (7). Also, they are speculated to have a mediational role in the microbiota-gut-brain axis crosstalk (8).

Only a small number of digestive microorganisms, including cellulolytic bacteria, have the capacity to break-down cellulose in the fermentative compartment (rumen and/or large intestine) of mammals (2,9).

Cellulolytic bacteria are considered as keystone species in the mammalian large intestine and rumen as they have the ability to initiate degradation of plant-cell walls and release energy sources on which the rest of the microbial community depends (9).

Cellulolytic bacteria are particularly sensitive to environmental changes associated to nutritional management (10, 11), medical management, and stressful events (12).

A reduction of cellulolytic bacteria has been related to dysbiosis, which in turn has been associated with diseases such as inflammatory bowel disease, colitis, chronic fatigue syndrome, obesity, and cancer. Maintaining fibrolysis is necessary for providing a balanced and healthy microbial ecosystem in the rumen and large intestine (13).

Bacteria fibrolysis in the digestive tract is crucial for the host nutrition, health and zootechnical performance. In some cases, enhancing bacteria fibrolysis in the digestive tract for increasing SCFAs production could be beneficial for the host nutrition, health and zootechnical performance.

It is the object of the present invention to provide new strains of cellulolytic bacteria as living microorganisms that could be fed in the diets of herbivores as well as omnivores for health, well-being, or performance concerns.

DETAILED INVENTION

The inventors recently isolated and characterized a strain of *Fibrobacter succinogenes*, called HC4, from equine cecal digesta. This strain notably shows a cellulolytic activity outside its original environment. In fact, it is cultivated on filter paper microcrystalline cellulose in a semi-synthetic medium (without digestive content) and the degradation of filter paper cellulose is observed as early as 14 hours of incubation. A growth on washed and ground hay as a sole source of carbon is also observed. The strain HC4 demonstrates higher total carboxy methylcellulase (CMCase) and xylanase activities when compared with *F. succinogenes* S85, the type species (Table 1).

Tests consisting of in vitro degradation of hay also notably demonstrated better results in presence of the strain HC4 when compared to a control without the strain, therefore demonstrating good probiotic potential of this *F. succinogenes* strain in improving the fibrolysis.

Therefore, the present invention relates to a bacterial strain of *Fibrobacter succinogenes* named HC4 that has been deposited on 17 Sep. 2020, at the German Collection of Microorganisms and Cell Cultures (DSMZ), Inhoffen-strasse 7B, 38124 Braunschweig, GERMANY, under the Budapest Treaty under number DSM 33656 (DSMZ 33656).

The present invention also concerns a composition comprising said bacterial strain.

Preferably, said composition is in the form of powder, pellet, granule, paste, cream or liquid such as a drinkable composition.

Even more preferably, the composition is an edible composition. The term "edible composition" is defined as a composition suitable or safe for eating.

The present invention also relates to the use of the bacterial strain of *Fibrobacter succinogenes* HC4 or a composition thereof as above described, as a probiotic.

The term "probiotic" is defined as a microorganism that when administered orally at adequate concentrations, provide a beneficial effect beyond that of their nutritional value, as defined by The Food and Agricultural Organization and World Health Organization.

In particular, said bacterial strain or said composition may be used to improve the digestive fibrolysis.

The term "fibrolysis" is defined as the degradation of fibers, including the degradation of the plant cell-walls fibers such as cellulose.

The term "digestive" qualifies the fibrolysis, which occurs in the rumen or large intestine depending on the mammalian subject.

By "improving", it means increasing the digestive fibrolysis with respect to a situation in absence of said strain or said composition.

The strain HC4 allows a better fiber digestibility in animals and humans. A more efficient fibrolysis allows:

a greater nutritional benefit from the feed, which can be of interest for animals and even for humans having a strict vegetarian regimen;

producing more metabolites of interest for health, which may be of interest for all mammals.

It also may have an impact on exercise performance or an improvement of zootechnical performance such as increasing milk production.

A beneficial effect on the subject's well-being and behavior can also be expected.

Thus, the improvement of the digestive fibrolysis due to the strain HC4 may have many beneficial effects on the subject regarding nutrition, condition, well-being or performance.

Thus, the present invention relates to the use of said bacterial strain or a composition comprising said bacterial strain as a probiotic. In healthy subjects, the present invention therefore relates to a non-therapeutic use of the strain HC4 or a composition thereof as previously described, as a probiotic.

"Healthy" means that the subject does not have any disease, in particular no disease associated to a digestive fibrolysis issue.

The uses of the bacterial strain of *Fibrobacter succinogenes* HC4 or a composition thereof described in the present disclosure, are intended to a mammalian subject.

In the present disclosure, the term "mammalian subject" includes both humans and mammalian animals. In particular, said mammalian animals are horses, sheep, cows, goats or pigs.

Thus, the invention relates to the use of said bacterial strain or a composition comprising said bacterial strain as a probiotic in a mammalian subject.

In particular, said use is to improve the digestive fibrolysis.

Therefore, the present invention relates to the use of said bacterial strain or a composition comprising said bacterial strain as a probiotic to improve or increase the digestive fibrolysis. In healthy subjects, the present invention relates to a non-therapeutic use of the bacterial strain HC4 or a composition comprising said bacterial strain as a probiotic to improve or increase the digestive fibrolysis, in particular in mammalian subjects.

In a more particular embodiment, the present invention relates to the use of the bacterial strain HC4 or a composition comprising said bacterial strain to improve or increase the digestive fibrolysis in mammalian animals such as horses, sheep, cows, goats or pigs.

A method for improving digestive fibrolysis is further disclosed. Said method comprises at least a step of administering said bacterial strain or said composition comprising the bacterial strain HC4 to a mammalian subject as previously defined.

In a particular embodiment, the present invention relates to the bacterial strain HC4 or a composition comprising said strain for use in the improvement or the increasing of the digestive fibrolysis, in particular in a mammalian subject as previously defined.

In a particular embodiment, the present invention relates to the bacterial strain HC4 or a composition comprising said strain for use as a probiotic, in particular in a mammalian subject as previously defined.

RESULTS

Identification of *F. succinogenes* Newly Isolated Strain HC4 from Cecal Digesta The HC4 strain of *F. succinogenes* was isolated from equine cecal samples after cultivation on filter paper cellulose. This strain has been deposited on 17 Sep. 2020, at the German Collection of Microorganisms and Cell Cultures (DSMZ), Inhoffenstrasse 7B, 38124 Braunschweig, GERMANY, under the Budapest Treaty, under number DSM 33656.

Figure 1:
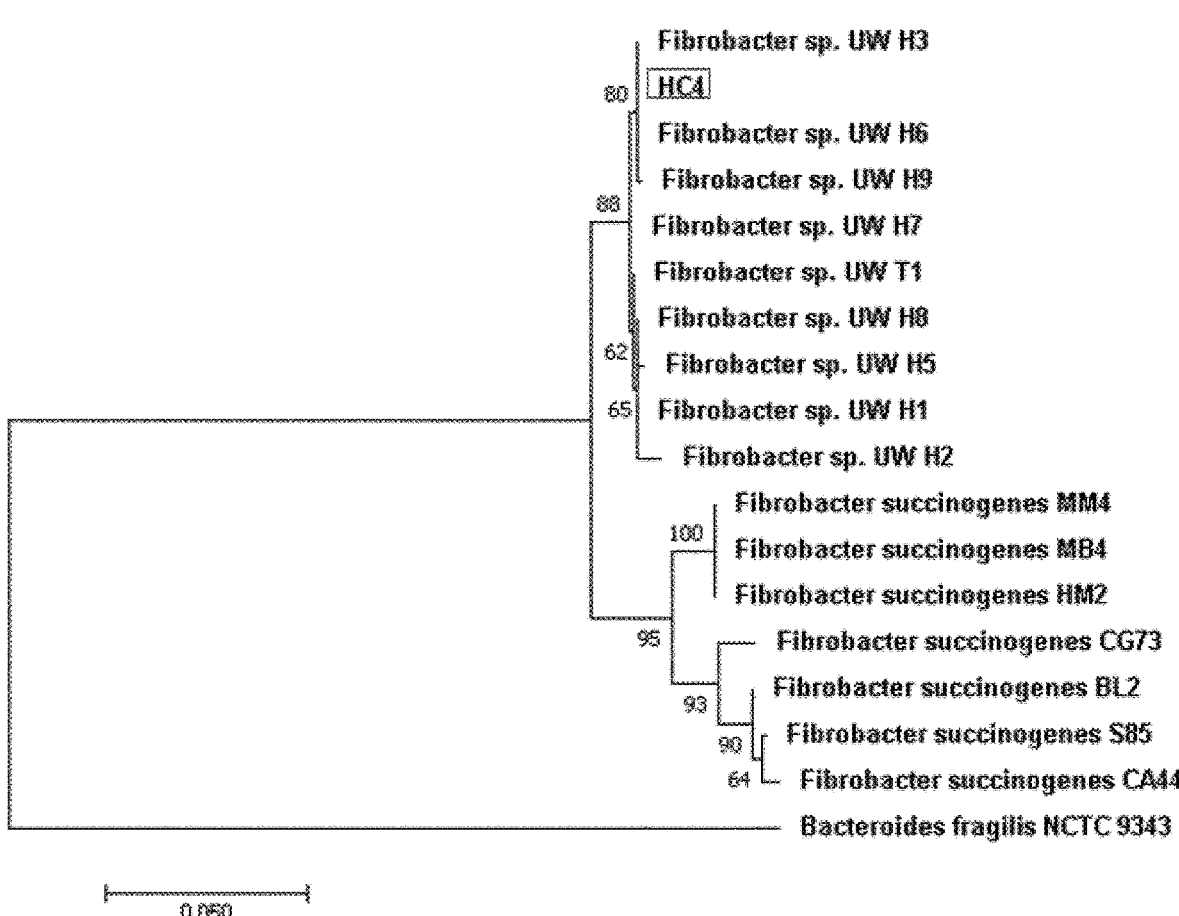
FIG. 1: Phylogenetic tree of *Fibrobacter* spp. by maximum likelihood method (1,000 bootstrap trial).

16S rRNA sequence analysis showed 99% similarity with *F. succinogenes* group V of newly isolated strains from feces of horses (14). The phylogenetic tree of *Fibrobacter* spp. with *Bacteroides fragilis* NCTC 9343 as an out group is show in FIG. 1. The numbers at each branch represent bootstrap values. The phylogeny tree was constructed using near-full length 16S ribosomal RNA sequence (1268 sites). Phenotypic and Metabolic Characteristics of *F. succinogenes* HC4

Figure 2:
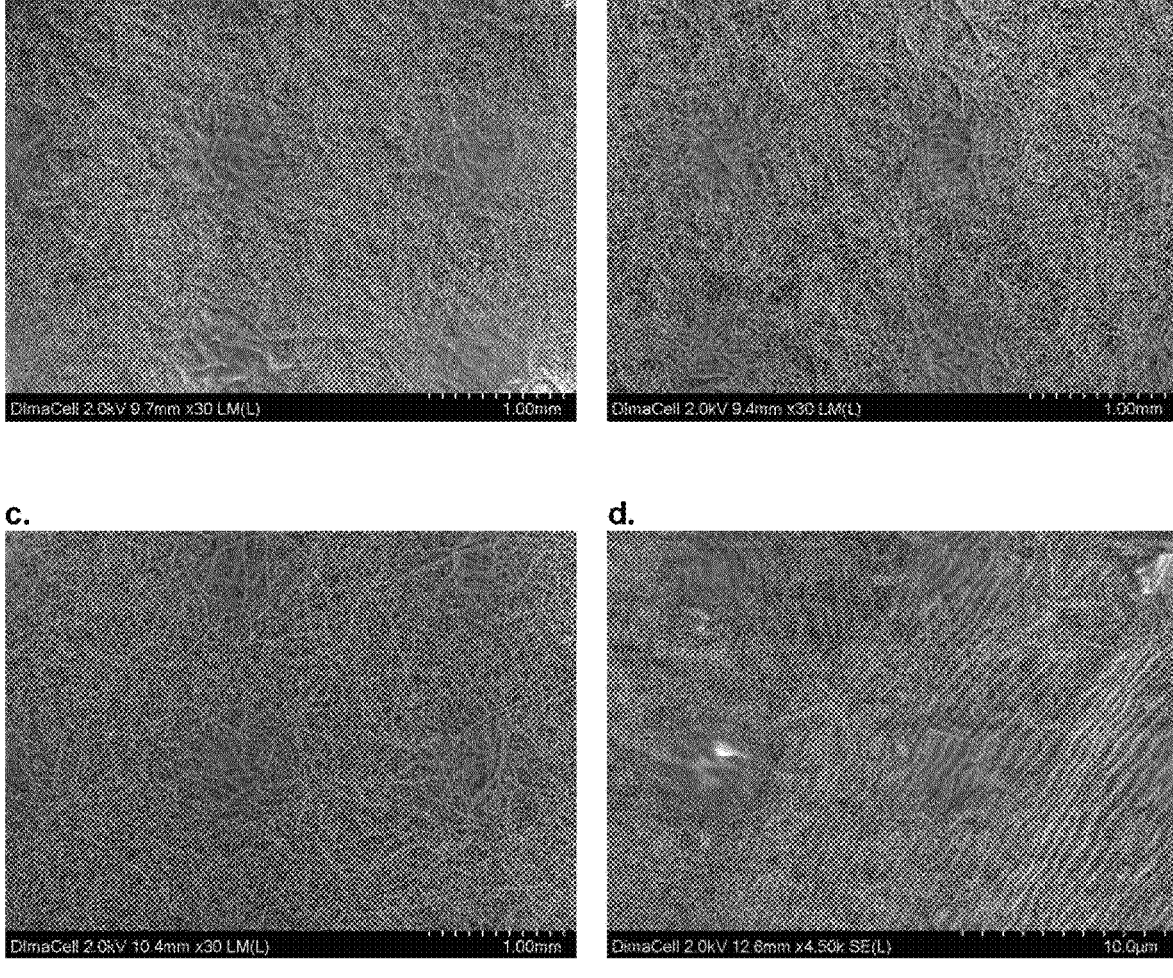
FIG. 2: SEM of filter paper cellulose without bacteria (a) and observation of strain *Fibrobacter succinogenes* HC4 cells on filter paper cellulose by SEM after 24 h (b) and 48 h (c, d) of culture.

Strain appeared as gram-negative rods or pleomorphic ovoid cells under the optic microscope. Attachment on filter paper cellulose was observed by scanning electron microscope (SEM) after a cryo-protection treatment (nitrogen gel at −140° C.) by DlmaCell (FIG. 2.*d*.). Rod cells of 2.1 μm in length and 0.65 μm in diameter were observed on cellulose fiber. The degradation of cellulose occurred as early as 24 hours, whereas nothing visible appeared to the naked eye at the same time. Filter paper was completely degraded after 48 hours (FIG. 2).

Figure 3:
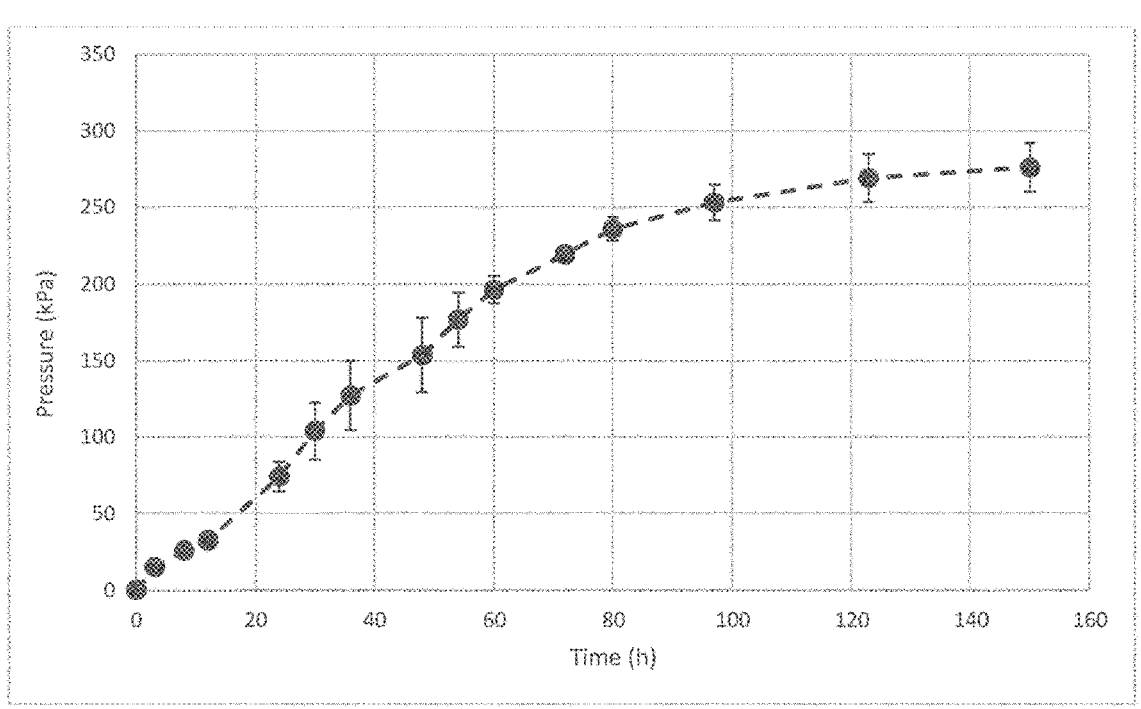
FIG. 3: Gas production kinetics by the strain HC4 with hay as sole source of C and N.

Strain HC4 grew on filter paper cellulose and on cellulose powder (Sigmacell® 50 cellulose-Sigma Chemicals) as the sole carbon source in the media. After optimising the growth of strain HC4, the degradation of cellulose was visible as early as 14 hours of incubation. It also revealed a growth on washed dried ground hay, as the sole source of carbon and nitrogen (FIG. 3), and showed 33.26% of dry matter disappearance (DMD) of hay after 150 hours of culture.

Figure 4:
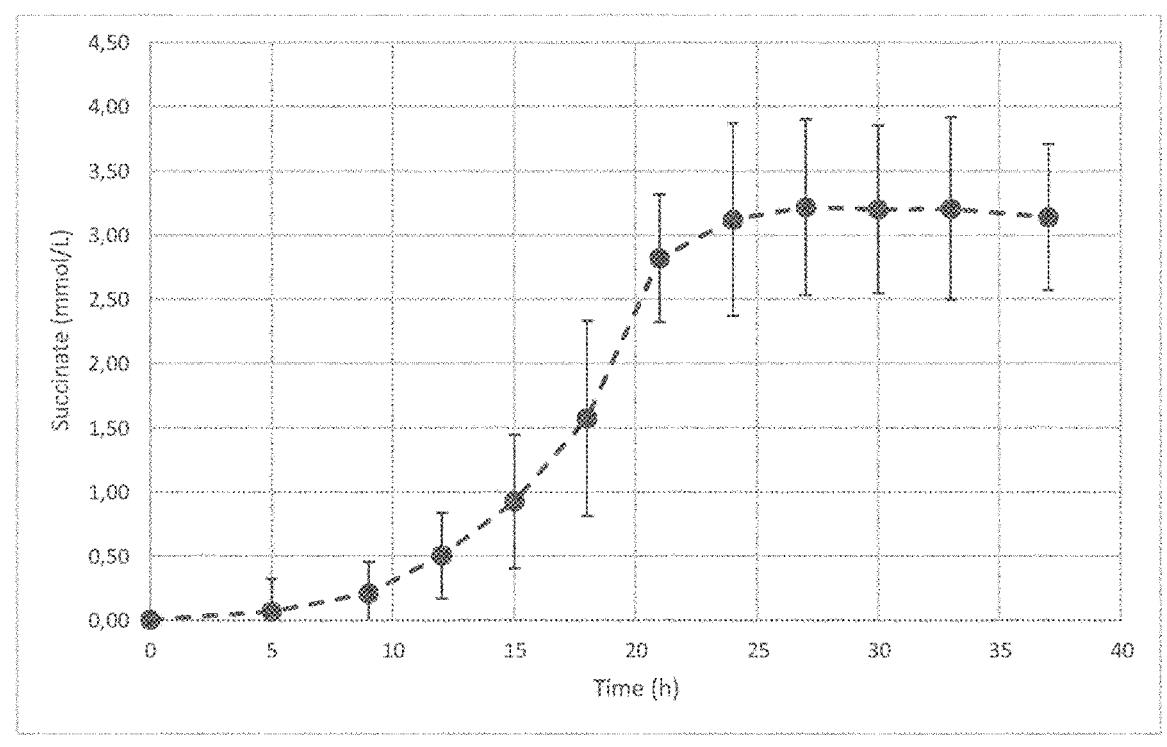
FIG. 4: Succinate production kinetics by the strain HC4 on filter paper cellulose.
Figure 5:
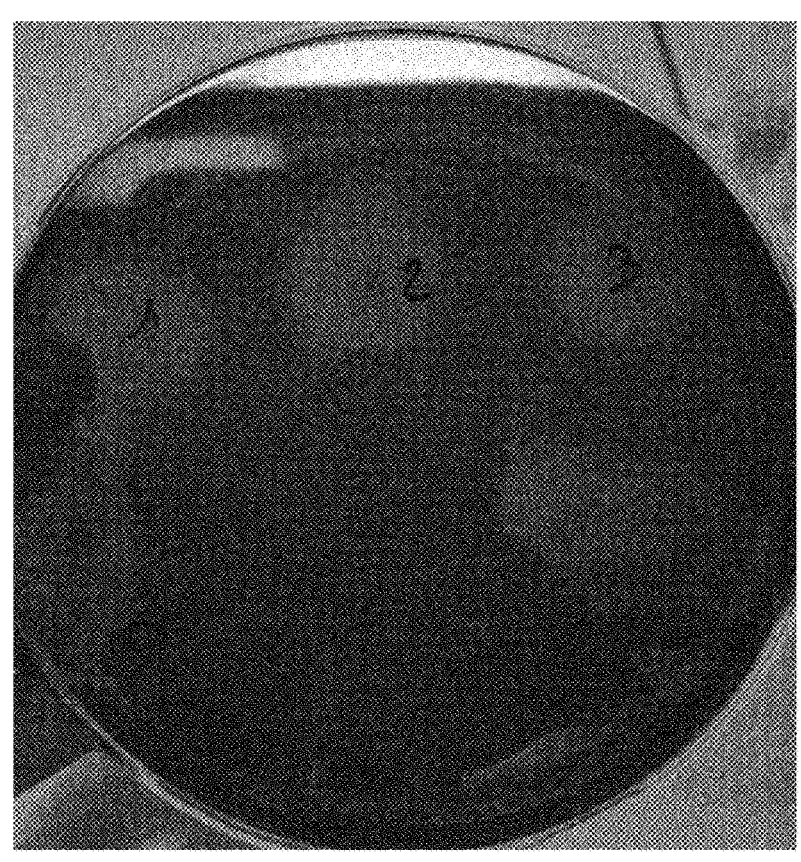
FIG. 5: CMCase activity of the strain HC4 by the Congo red method.

Strain HC4 consumed glucose and cellobiose. No growth was observed on raffinose, maltose, lactose, xylose, mannose, rhamnose, arabinose, sucrose, galactose, melezitose, mannitol, sorbitol and on beechwood xylan. After 48-hours cultures on filter paper cellulose at 38° C., it produced succinate (47.02 μmol/mg of protein) and acetate (45.69 μmol/mg of protein). The stationary growth phase of HC4 was reached after 22 h by measuring the produce of succinate by the strain (FIG. 4). Cultures reached cell densities $10^8$ viable cells per ml on filter paper cellulose. *F. succinogenes* HC4 did not survive after 1 hour contact with oxygen. Detection and Quantification of Cellulase and Xylanase Activities Using Congo red, strain HC4 showed a fibrolytic activity on carboxymethyl cellulose (CMC) (FIG. 5), beechwood xylan and dried ground hay as sole substrate. The CMCase and xylanase activities were quantified with CMC or beechwood xylan as substrate and compared with *F. succinogenes* S85, the type species (Table 1). Similar intracellular CMCase activities were measured for *F. succinogenes* HC4 and S85 while extracellular CMCase activity of HC4 was higher than that of S85. Intracellular xylanase activity of HC4 was lower than that of S85 but extracellular activity of HC4 was highest. Therefore, total CMCase and xylanase activities were highest for HC4. For the both strains, fibrolytic activities were most extracellular.

TABLE 1

Enzyme specific activities on bacteria grown on cellulose

|  | CMCase activity (nkat glucose eq/ mg of protein) | | Xylanase activity (nkat xylose eq/ mg of protein) | |
| --- | --- | --- | --- | --- |
|  | Intra- cellular | Extra- cellular | Intra- cellular | Extra- cellular |
| *F. succinogenes* HC4 | 8.47 ± 1.28 | 88.28 ± 17.47 | 5.75 ± 0.46 | 51.38 ± 3.73 |
| *F. succinogenes* S85 | 6.79 ± 0.71 | 25.07 ± 2.89 | 10.44 ± 1.27 | 34.29 ± 4.92 |

Identification of Genes Involved:

Oxidative stress resistance: Genome encodes thioredoxin reductase, enzyme to counter oxidative stress. No superoxide dismutase and catalase were identified.

Anaerobe respiration and carbon metabolism: Strain HC4 genome lacked major components of the electron transport chain, making impossible the use of $O_2$ to grow. One gene coding cellobiose phosphorylase was found to degrade cellobiose in glucose-1-phosphate. All genes allowing the glycolysis pathway were identified to the use of glucose until the production of phosphoenoylpyruvate (PEP). *F. succinogenes* HC4 genome contained genes coding PEP carboxykinase and pyruvate kinase to transform PEP in pyruvate or in oxaloacetate respectively. The gene for pyruvate carboxylase, to transform pyruvate in oxaloacetate, was also identified. Not all of genes that allow tricarboxylic acid (TCA) cycle have been identified. *F. succinogenese* HC4 lacked genes coding for enzymes α-ketoglutarate dehydrogenase and succinyl-CoA synthetase, suggesting the use of an incomplete and reductive TCA cycle by HC4. Genes for pyruvate-flavodoxin oxidoreducatase, acetyl-coenzyme A synthetase, phosphate acetyltransferase and acetate kinase were also identified. The gene for formate C-acetyltransferase was missing. Genes of the nonoxidative branch of the pentose phosphate pathway were identified but not those to the oxidative branch. No xylose metabolizing enzymes (xylose isomerase, xylulokinase, xylose permease) were predicted either.

N metabolism: No gene coding for the N fixation was found in the genome of HC4. It is known fact that *Fibrobacter succinogenes* requires ammonia as source of N (15). Genes for ammonia transporter and its assimilation were identified: glutamate synthase, glutamate deshydrogenase, histidine ammonia lyase and carbamoyl-phosphate synthase. Genome of HC4 also contained the gene for glutamine synthetase. Additionally, two ureases subunits and four urease accessory proteins were predicted.

In Vitro Degradation of Hay

Figure 6:
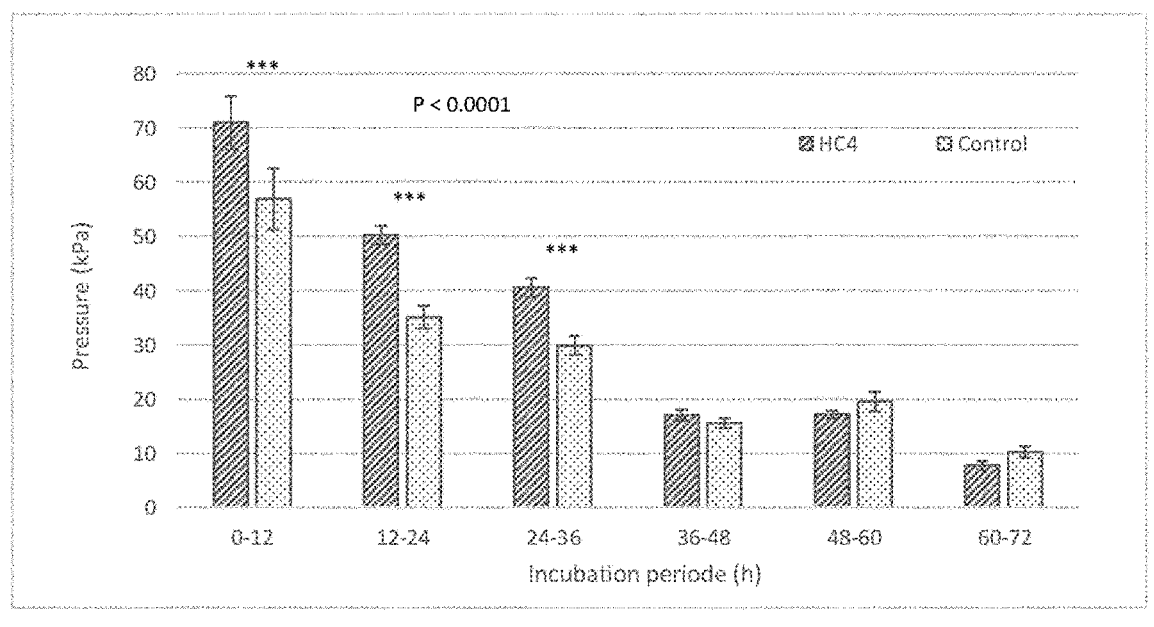
FIG. 6: In vitro gas production rate every 12 h. , $P<0.01$; *, $P<0.0001$ versus control.
Figure 7:
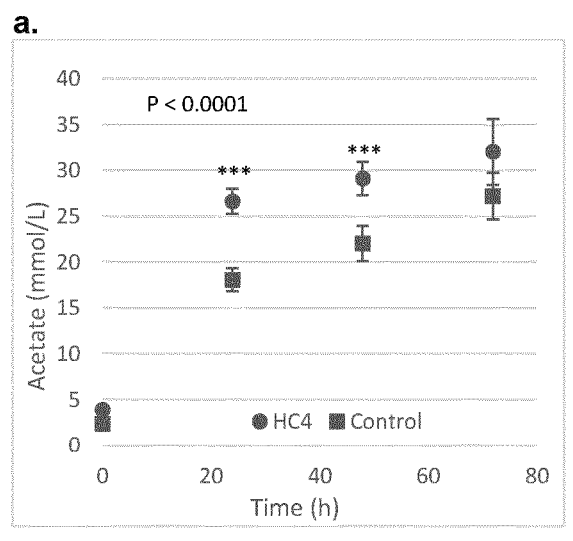
FIG. 7: In vitro production of acetate (a), propionate (b), butyrate (c), valerate (d). , $P<0.01$; *, $P<0.0001$ versus control.
Figure 7:
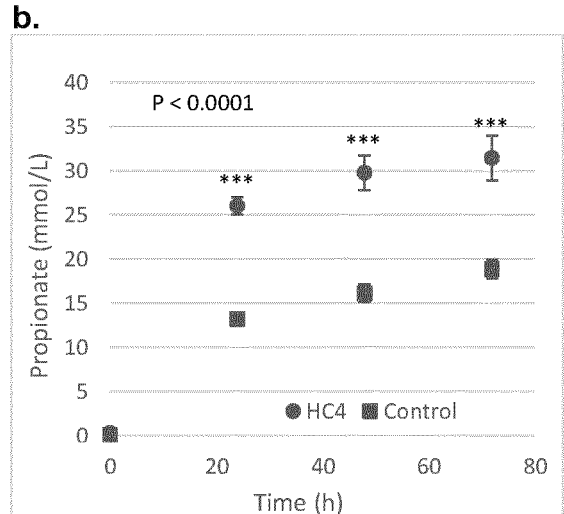
Figure 7:
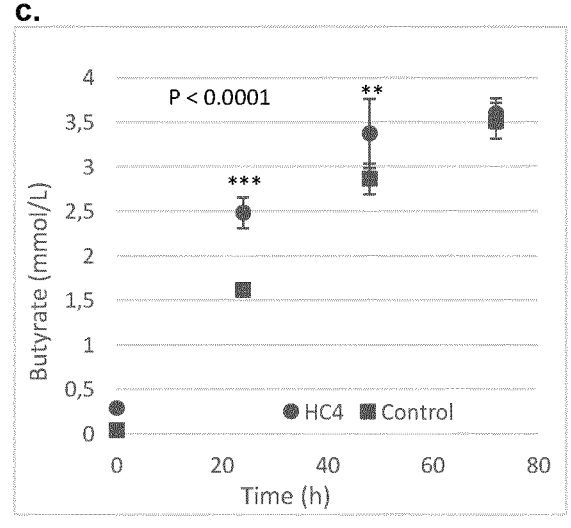
Figure 7:
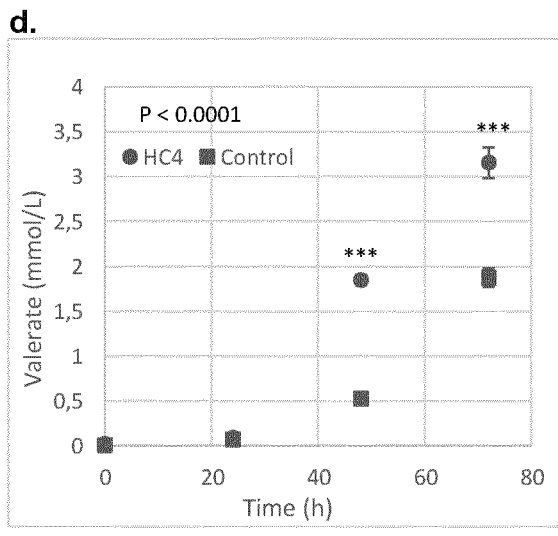
Figure 8:
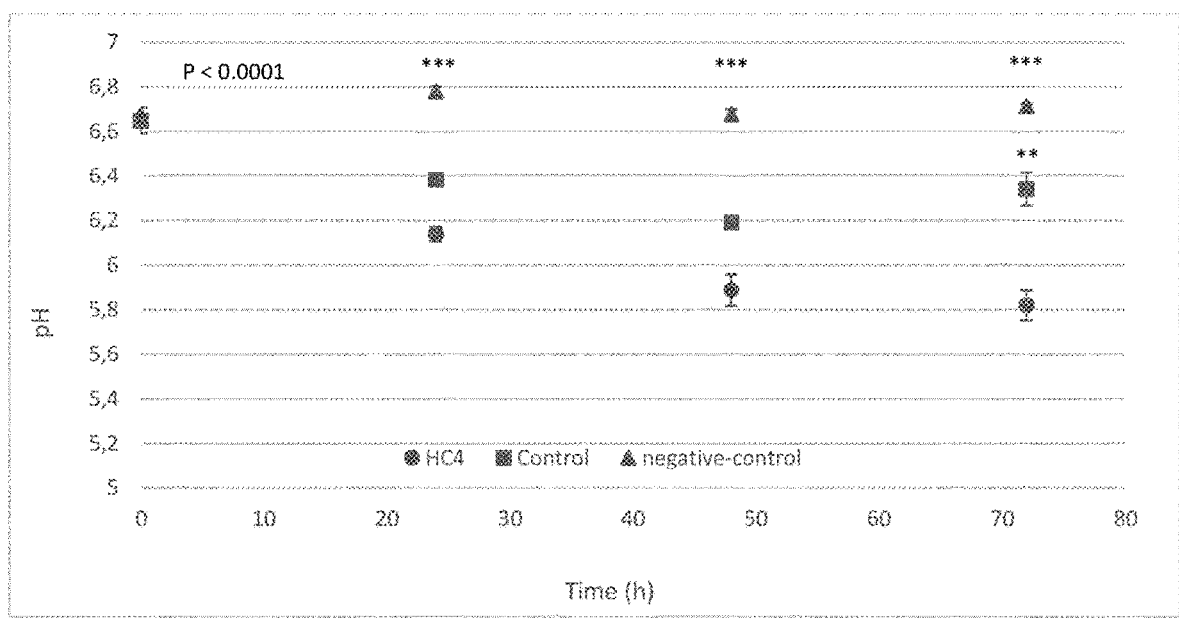
FIG. 8: pH evolution during the in vitro test. , $P<0.01$; *, $P<0.0001$ versus control and negative control.
Figure 9:
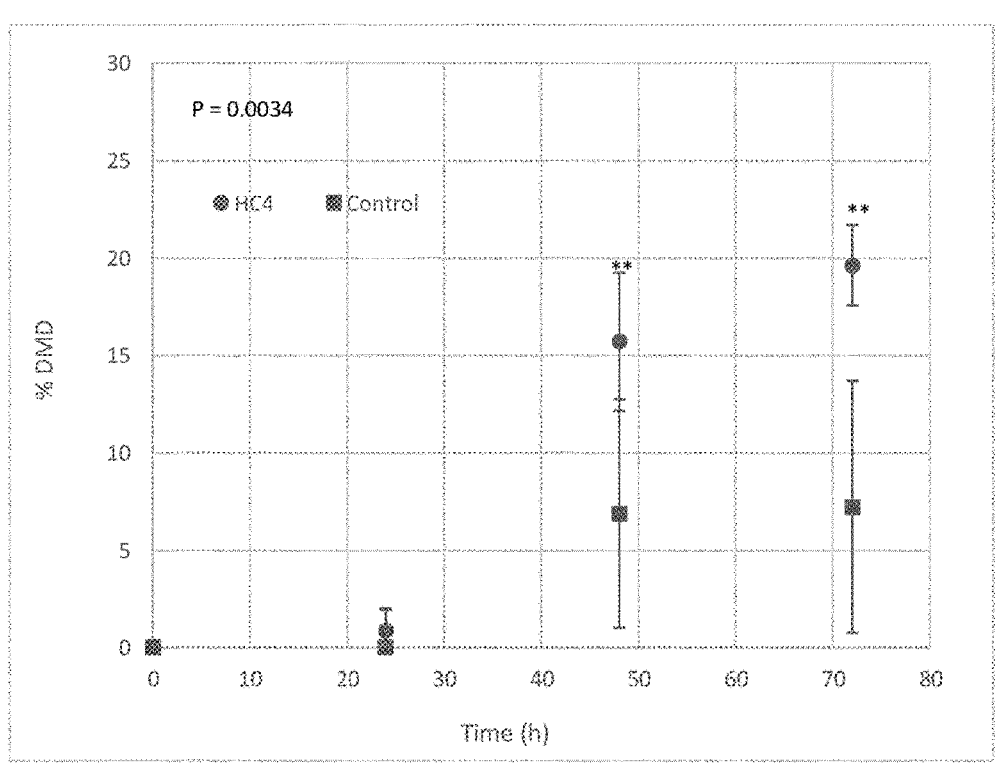
FIG. 9: % DMD evolution during the in vitro test. , $P<0.01$; *, $P<0.0001$ versus control.

To investigate probiotic potential of *F. succinogenes* HC4 in case of large intestinal dysbiosis, the effect of strain HC4 was studied in vitro on equine fecal microbial activity. The feces used as inoculum contained $2.18 \times 10^8$ UFC/g of total cultivable bacteria with only $2 \times 10^5$ MPN/g cellulolytic bacteria (Table 2). Adding *F. succinogenes* HC4 at $7.7 \times 10^7$ MPN/mL increased significantly gas production (P<0.0001) compared to the control without the strain HC4 (FIG. 6). This difference started in the first hours up to 36 hours. The beginning of the stationary phase was observed from 72 hours whereas in the control flasks gas was still produced tending to reach the amount produced with HC4. Additionally, when HC4 was present, more VFAs were produced (FIG. 7). Acetate, butyrate and propionate concentrations were higher at 24 h, 48 h but the quantity of acetate, butyrate with the control reached the one with HC4 at 72 h. Higher concentration of valerate was produced from 48 h to 72 h when HC4 was added. No lactate was measured. According to these results, the pH decreased more rapidly when HC4 was present (FIG. 8). Between 48 h and 72 h, the pH of the cultures with HC4 was stable whereas it increased in the control. Likewise, the DMD was more important at 48 and 72 h with HC4 (FIG. 9). At 48 h, there were 16% of DMD with HC4 against 7% in the control without HC4. At 72 h, there were 20% with HC4 whereas the DMD was always at 7% in the control.

TABLE 2

Composition for 1 g of added faeces

| | |
| --- | --- |
| Total cultivable anaerobic bacteria (CFU) | $2.18 \times 10^8$ |
| Amylolytic bacteria (CFU) | $3.40 \times 10^7$ |
| Lactate-utilizers (CFU) | $2.07 \times 10^7$ |
| Cellulolytic bacteria (MPN) | $2.00 \times 10^5$ |
| Lactate (μmol) | 1.34 |
| Acetate (μmol) | 28.3 |
| Propionate (μmol) | 9.79 |
| Butyrate (μmol) | 2.27 |
| Valerate (μmol) | 0.980 |

Safety of *F. succinogenes* HC4

Antibiotic Resistance and Virulence Genes

No antibiotic resistance gene in the genome of strain HC4 was predicted by the MicroScope platform.

Two genes potentially involved in virulence were identified by the MicroScope platform. However, the percentage of identity with the genes of other bacteria involved in virulence was low (between 30 and 34%).

The first gene was identified as M protein, but this function is only known in Gram-positive bacteria, which is not the case for HC4.

Five possible annotations were found for the second gene potentially involved in virulence. These annotations corresponded to response regulators involved in the mobility of pathogenic bacteria (CheY, PilH, PilG, CheY). The strain HC4 is not mobile, this gene identified as response regulator seems to have another function.

Phenotypic Tests for Antibiotic Resistance

The concentration allowing the inhibition of the growth of the HC4 strain was identified for each antibiotic (Table 3).

TABLE 3

| Concentrations inhibiting the growth of *F. succinogenes* HC4 | |
|---|---|
| Antibiotics: | Concentrations to inhibit growth (mg/L): |
| Ampicillin | 32 |
| Gentamicin | 128 |
| Kanamycin | 8000 |
| Streptomycin | 2048 |
| Tetracyclin | 1 |
| Ciprofloxacin | 0.25 |
| Colistin | 64 |
| Fosfomycin | 512 |

Conclusion of Safety

No antibiotic resistance genes were identified in strain HC4. All antibiotics tested had an inhibitory effect on the growth of the strain HC4. The concentration allowing the inhibition is antibiotic-dependent. These tests being performed in liquid medium because of the anaerobic conditions are hardly comparable to what is already known and tested on solid medium.

The genes potentially involved in virulence found in the genome of strain HC4 do not seem to be of concern.

Materials and Methods

Sample Collection and Enrichment of Filter Paper Degrading Bacteria

Caecum digesta were collected from one horse and transported back to the laboratory for same day inoculation, typically less than four hours post collection. One gram of collected sample was diluted 10-fold in an anaerobic mineral solution (16). Serial 10-fold dilutions down to $10^{-8}$ were carried out. All liquid and solid media were prepared, dispensed and inoculated using strictly anaerobic techniques (17). Each dilution was inoculated in specific medium for cellulolytic bacteria (18) containing filter paper as cellulose source and modified by Julliand et al. (19).

Cellulolytic Bacteria Isolation

After incubation at 38° C. under anaerobic atmosphere for 7 days, two isolation methods were used from the highest dilution showing filter paper degradation: first the roll tubes method described by Hungate in 1969 (20) and then the enrichment method recently published by Neumann et al., 2017 (14).

Morphological and Genetic Identification (Sequencing of 16S rRNA Genes) of Cellulolytic Isolates Isolated strains were examined for purity, morphology and Gram staining by phase contrast microscopy in semi-synthetic medium with 2% Sigmacell® or piece of filter paper cellulose grown culture. Bacterial DNA was extracted using DNA extraction kit (Instagene Matrix—732-6030, Biorad, Hercules, California, United States). The 16S rRNA gene were amplified with universal primers 27f (5'-AGAGTTTGATCMTGGCTCAG-3') (SEQ ID NO:1) and 1492r (5'-TACGGHTACCTTGTTACGACTT-3') (SEQ ID NO:2). As a reminder, in the field of molecular biology nucleotide M corresponds to A or C, and nucleotide H corresponds to A or C or T.

Amplification products were confirmed by gel electrophoreses. Subsequently, PCR products were sequenced by Genewiz using the Sanger method. Sequences were analysed using BLAST from the National Center of Biotechnology Information (NCBI) website.

A maximum likelihood phylogenetic tree was established from full-length 16SRNA gene sequences in MEGA 7.0 using 1,000 bootstrap replicates. A 16S rRNA gene sequence from *Bacteroides fragilis* type strain NCTC 9343 was included as an outgroup.

Enzymatic Activity of Isolated Cellulolytic Bacteria

The fibrolytic activity was detected with Congo red. 48-hours cultures of isolated bacteria were deposited (10 µL) on agar plate with 0.5% of CMC (CMC sodium salt, medium viscosity, Sigma-Aldrich, St. Louis, Missouri, United States), with 0.3% of dried ground hay or with 0.3% of beechwood xylan (Megazyme International Ireland Ltd., Wicklow, Ireland) in an anaerobic glove bag with a gas phase of 5% H2, 10% Co2 and 85% N2. After incubation at 38° C. for 24 h, agar plates were strained with Congo red 0.2% to detected cellulolytic activity (21).

Bacterial enzymes were extracted from 48-hours isolated strain cultures on filter paper semi-synthetic medium. The supernatants were kept frozen at −20° C. The cell pellets were suspended, and membranes were made vulnerable by two freezing/defrosting cycles and then broken by sonication. The supernatants containing enzymes intra-cellular were harvested after centrifugation and kept frozen at −20° C.

All cultures were performed in triplicate to determine the CMCase and xylanase activities assessed by incubating enzymes preparations with CMC or xylan from beechwood (22). Results are given in nanokatals, where 1 kat corresponds to 1 mol of glucose equivalent produce per seconds.

Soluble proteins were determined using bovine serum albumin (Sigma-Aldrich, St. Louis, Missouri, United States) as the standard (23).

O2 Sensitivity $O_2$ sensitivity was tested in aerobic condition (without adding $CO_2$) during 2 min, 1 h, 5 h, and 24 h at 38° C. Growth was verified by the degradation of filter paper by bacteria. All cultures were performed in triplicate.

Substrates Consumed and Degraded

Isolated strain was cultured in Lowe semi-synthetic medium (24) in which carbon source was substituted by glucose, cellobiose, xylose, lactose, raffinose, maltose, mannose, or rhamnose. Growth was monitored by gas production, optical density (DO) (CECIL 1011, Cecil Instrumentation Services Ltd, Cambridge, England) and by pH. Growth on crystalline cellulose was investigated too using the same medium with Sigmacell® replacing cellobiose and was monitored by visual observation of the culture tube, by increased turbidity and gas production. The growth on washed dried ground hay, as sole source of C and N, in the same medium used for the in vitro digestibility in flask anaerobic with gas impermeable butyl stopper and aluminium crimp seals was explored by following gas production and DMS was measured after 150 hours at 38° C. All cultures were performed in triplicate.

Metabolic Product Analysis

Fermentation products present in culture with filter paper were quantified after 48 hours. VFAs, Acetate (C2), Propionate (C3), Butyrate (C4), Valerate (C5) concentrations were assayed by a gas chromatography (GC) (Gas chromatograph-flam ionization detector Clarus 500, PerkinElmer, Courtaboeuf, France) (25). Succinic and formic acid concentrations were measured spectrophotometrically at 340 nm (MRX revelation, Dynatech Laboratories, Guyancourt, France) in microplate using an enzymatic colorimetric method (Succinic acid Assay Kit, Formic Acid Assay kit, Megazyme International Ireland Ltd., Wicklow, Ireland).

Complete Genome Sequencing, Assembly and Annotation

After DNA extraction, the whole genome of *F. succinogenes* HC4 was sequenced, assembled and annotated by Genewiz, Germany. Libraries were performed with NEBNext Ultra II DNA library preparation kit for Illumina and sequenced using an Illumina NovaSeq 2×150 bp sequencing platform. De novo assembly was carried out using SPAdes v3.10.0 (K-mer length of 21, 33, 55, 77) (26). QUAST (27) was used to generate statistics for the de novo assembled genome. The prediction and annotation of genes were performed using the Prokka v1.12 (28) with ISfinder, NCBI Bacterial Antimicrobial Resistance Reference Gene Database, and UniProtKB databases.

In Vitro Digestibility and Gas Production

The effect of the new isolated strain HC4 was studied in vitro on equine fecal microbial activity. Fecal inoculum was obtained from three horses submitted to an abrupt change of diet from a high fiber to the high starch diet and after 5 days on 60% hay-40% concentrate diet. Feces were collected from the rectum. Fifty mL of modified Lowe medium (no substrate, no growth factors) (24), and 1 g of sterile dried ground hay previously washed as only carbon source were incubated with 1 g fecal inoculum and 10 mL of selected cellulolytic bacteria culture. Washed hay contained (g/kg DM) the following: OM: 96.6, CP: 67.68, NDF: 480.39, ADF: 759.27, and WSC: 71.21.

Culture of the isolated cellulolytic strain monitored by succinate assay allowed the harvest of the strain during the exponential growth phase in Lowe medium containing filter paper.

Concentration of total cultivable anaerobic bacteria were determined using four replicate roll tubes (20) prepared with dilutions representing $10^{-5}$, $10^{-6}$, $10^{-7}$ mL of intestinal contents on a non-selective modified complete agar medium [46; 5] after 48 h of incubation at 38° C. Concentrations of lactate-utilising bacteria were determined by the same method on a selective medium (29) after 48 h of incubation at 38° C. Concentrations of starch-utilising bacteria were determined on a modified selective medium containing soluble starch as the main energy source (24) after 48 h of incubation at 38° C. The most probable number (MPN) (30) of cellulolytic bacteria (dilutions representing $10^{-3}$, $10^{-4}$, $10^{-5}$ and $10^{-6}$ of intestinal contents) was determined using the modified broth medium (Halliwell & Bryant, 1963; Julliand et al., 1999) after 15 days of incubation at 38° C. The same method was used to determine the MPN of the isolated cellulolytic bacteria inoculum with dilutions representing $10^{-7}$, $10^{-8}$ and $10^{-9}$ of bacterial culture.

Two controls were carried out in vitro: one with hay and fecal inoculum and one negative with only fecal inoculum. Each condition was replicated three times and incubated at 38° C. Growth was monitored following gas production at 3, 8, 12, 24, 30, 36, 48, 54, 60, 72, 80, 97, 123 and 150 h. The pressure measures from same flasks were used to calculate the gas accumulation at each time and to know the gas production between two times. During the first 72 h of the incubation and every 24 h, pH, DMD after 24 h at 80° C. and concentrations of SCFAs (acetate, propionate, iso-butyrate, butyrate, iso-valerate, valerate, D- and L-lactate) were measured on three cultures for each condition. The assay of VFAs was carried by GC and D-lactate and L-lactate concentrations were measured using an enzymatic colorimetric method (Megazyme, D-/L-Lactic Acid (D-/L-Lactate) (Rapid) Assay Kit, Megazyme International Ireland Ltd., Wicklow, Ireland) as explained in the previous paragraphs. A mixed procedure (SAS) was used to evaluate the effect of the strain dose and time of fermentation. Significance was declared at <0.05.

Safety Study

Investigation of antibiotic resistance and virulence genes

From the sequenced genome of the strain HC4, antibiotic resistance and virulence genes were investigated through the platform MicroScope (Microbial Genome Annotation &

Analysis Platform, hypertext transfer protocol secure:// mage.genoscope.cns.fr/microscope/home/index.php).

Phenotypic Tests for Antibiotic Resistance

Eight antibiotics were tested according to EFSA recommendations for Gram-negative bacteria (31). Before being added to the filter paper semi-synthetic medium, the antibiotics were sterilized by filtration (0.22 μm filters).

24-hours cultures of strain HC4 were inoculated into media containing each antibiotic. A positive control without antibiotics was inoculated from the same culture of strain HC4 and two cultures were prepared for each condition. After 48 hours of incubation at 38° C., the observation of filter paper degradation allowed estimating the bacterial growth. In case of no degradation, a sample of liquid was taken and frozen at −20° C. for further determination of succinate production.

BIBLIOGRAPHY

1. Flint H J, Scott K P, Louis P, Duncan S H. The role of the gut microbiota in nutrition and health. Nat Rev Gastroenterol Hepatol. 2012; 9(10): 577-89.
2. Flint H J, Scott K P, Duncan S H, Louis P, Forano E. Microbial degradation of complex carbohydrates in the gut. Gut Microbes. 2012; 3(4): 289-306.
3. Bergman E N. Energy contributions of volatile fatty acids from the gastrointestinal tract in various species. Physiol Rev. 1990; 70(2): 567-90.
4. Argenzio R A. Functions of the equine large intestine and their interrelationship in disease. Cornell Vet. 1975; 65(3): 303-30.
5. Varel V H, Yen J T. Microbial perspective on fiber utilization by swine. J Anim Sci. 1997; 75(10): 2715-22.
6. McNeil N I. The contribution of the large-intestine to energy supplies in man. Am J Clin Nutr. 1984; 39(2): 338-42.
7. Blaak E E, Canfora E E, Theis S, Frost G, Groen A K, Mithieux G, et al. Short chain fatty acids in human gut and metabolic health. Benef Microbes. 2020; 11(5): 411-55.
8. Dalile B, Oudenhove L Van, Vervliet B, Verbeke K. The role of short-chain fatty acids in microbiota-gut-brain communication. Nat Rev Gastroenterol Hepatol. 2019; 16(8): 461-78.
9. Ze X, Le Mougen F, Duncan S H, Louis P, Flints H J. Some are more equal than others: the role of "keystone" species in the degradation of recalcitrant substrates. Gut Microbes. 2013; 4(3): 236-40.
10. Julliand V, Grimm P. The Impact of Diet on the Hindgut Microbiome. J Equine Vet Sci. 2017; 52:23-8.
11. Varel V H, Robinson I M, Jung H J G. Influence of dietary fiber on xylanolytic and cellulolytic bacteria of adult pigs. Appl Environ Microbiol. 1987; 53(1): 22-6.
12. Flint H J. Why Gut Microbes Matter: Understanding our microbiome. 2020. 97-108 p. Available from: https://link.springer.com/chapter/10.1007/978-3-030-43246-1_8
13. Thomas S, Lucie E-M, Adeline S, Pascale M, Christophe M C, Tom V de W, et al. Tripartite relationship between gut microbiota, intestinal mucus and dietary fibers: towards preventive strategies against enteric infections. FEMS Microbiol Rev. 2020
14. Neumann A P, McCormick C A, Suen G. Fibrobacter communities in the gastrointestinal tracts of diverse hindgut-fermenting herbivores are distinct from those of the rumen. Environ Microbiol. 2017; 19(9): 3768-83.
15. Bryant M P, Robinson I M, Chu H. Observations on the nutrition of bacteroides succinogenes—a ruminal cellulolytic bacterium. J Dairy Sci. 1959; 42(11): 1831-47.

16. Bryant M P, Burkey L A. Cultural methods and some characteristics of some of the more numerous groups of bacteria in the bovine rumen. J Dairy Sci. 1953; 36(3): 205-17.

17. Hungate R E. The anaerobic mesophilic cellulolytic bacteria. Bacteriol Rev. 1950; 14(1): 1-49.

18. Halliwell G, Bryant M P. The cellulolytic activity of pure strains of bacteria from the rumen of cattle. J Gen Microbiol. 1963; 32(1963): 441-8.

19. Julliand V, De Vaux A, Millet L, Fonty G. Identification of Ruminococcus flavefaciens as the predominant cellulolytic bacterial species of the equine cecum. Appl Environ Microbiol. 1999; 65(8): 3738-41.

20. Hungate R E. Chapter IV A roll tube method for cultivation of strict anaerobes. Methods Microbiol. 1969; 3:117-32.

27. Gurevich A, Saveliev V, Vyahhi N, Tesler G. QUAST: Quality assessment tool for genome assemblies. Bioinformatics. 2013; 29(8): 1072-5.

28. Seemann T. Prokka: Rapid prokaryotic genome annotation. Bioinformatics. 2014; 30(14): 2068-9.

29. Mackie R I, Heath S. Enumeration and isolation of lactate-utilizing bacteria from the rumen of sheep. Appl Environ Microbiol. 1979; 38(3): 416-21.

30. Clarke K R, Owens N J P. A simple and versatile micro-computer program for the determination of "most probable number. J Microbiol Methods. 1983; 1(3): 133-7.

31. EFSA FEEDAP Panel (2018). Guidance on the characterisation of microorganisms used as feed additives or as production organisms. EFSA Journal 16, 5206.

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial sequence
<220> FEATURE:
<223> OTHER INFORMATION: Synthetic Primer

<400> SEQUENCE: 1
agagtttgat cmtggctcag                                                20

<210> SEQ ID NO 2
<211> LENGTH: 22
<212> TYPE: DNA
<213> ORGANISM: Artificial sequence
<220> FEATURE:
<223> OTHER INFORMATION: Synthetic Primer

<400> SEQUENCE: 2
tacgghtacc ttgttacgac tt                                             22
```

21. Forano E, Broussolle V, Gaudet G, Bryant J A. Molecular cloning, expression, and characterization of a new endoglucanase gene from Fibrobacter succinogenes S85. Curr Microbiol. 1994; 28(1): 7-14.

22. Béra-Maillet C, Ribot Y, Forano E. Fiber-Degrading Systems of Different Strains of the Genus Fibrobacter. Appl Environ Microbiol. 2004; 70(4): 2172-9.

23. Bradford M M. A rapid and sensitive method for the quantitation of microgram quantities of protein utilizing the principle of protein-dye binding. Anal Biochem. 1976; 72(1-2): 248-54

24. Lowe S E, Theodorou M K, Trinci A P J, Hespell R B. Growth of anaerobic rumen fungi on defined and semi-defined media lacking rumen fluid. J Gen Microbiol. 1985; 131(9): 2225-9.

25. Jouany J P. Volatile fatty acid and alcohol determination in digestive contents, silage juices, bacterial cultures and anaerobic fermentor contents. Sciences des Aliments. 1982; 2:31-44.

26. Bankevich A, Nurk S, Antipov D, Gurevich A A, Dvorkin M, Kulikov A S, et al. SPAdes: A new genome assembly algorithm and its applications to single-cell sequencing. J Comput Biol. 2012; 19(5): 455-77.

The invention claimed is:

1. A composition comprising an isolated strain of *Fibrobacter succinogenes* deposited under the accession number DSM 33656, wherein the *Fibrobacter succinogenes* strain shows cellulolytic activity outside its original environment and wherein the *Fibrobacter succinogenes* strain is present at a concentration that is adequate to provide a probiotic effect, wherein the composition is an edible composition which is in the form of a cream, granule, paste or pellet.

2. The composition of claim 1, wherein the composition is an oral composition.

3. The composition of claim 1, wherein the composition is formulated as a probiotic composition.

4. The composition of claim 1, wherein the *Fibrobacter succinogenes* strain has higher extracellular carboxymethylcellulase and xylanase activities compared to *Fibrobacter succinogenes* S85 strain grown on cellulose.

5. A method for improving the digestive fibrolysis in a mammalian animal comprising orally administering to said animal the composition of claim 1.

6. The method of claim 5, wherein the mammalian animal is a human or a non-human animal.

7. The method of claim 6, wherein the non-human animal is a horse, a sheep, a cow, a goat, or a pig.

* * * * *